United States Patent [19]

Dombrowski

[11] Patent Number: 4,660,570
[45] Date of Patent: Apr. 28, 1987

[54] FETAL BLOOD SAMPLING INSTRUMENT

[76] Inventor: Mitchell P. Dombrowski, 103 Mapleton, Grosse Point Farms, Mich. 48236

[21] Appl. No.: 906,561

[22] Filed: Sep. 8, 1986

Related U.S. Application Data

[63] Continuation of Ser. No. 679,233, Dec. 7, 1984, abandoned, which is a continuation-in-part of Ser. No. 625,738, Jun. 28, 1984, abandoned.

[51] Int. Cl.$^4$ .............................................. A61B 5/00
[52] U.S. Cl. .................................... 128/765; 128/770; 604/272; 604/411
[58] Field of Search .................. 128/763–770, 128/698; 604/14–16, 21, 51, 54, 55, 115, 133, 264, 272, 327, 330, 331, 403, 411

[56] References Cited

U.S. PATENT DOCUMENTS

| | | | |
|---|---|---|---|
| 1,147,408 | 7/1915 | Kells | 604/272 |
| 3,162,195 | 12/1964 | Dick | 128/766 |
| 3,401,689 | 9/1968 | Greenwood | 604/55 |
| 3,572,335 | 3/1971 | Robinson | 604/55 |
| 3,685,509 | 8/1972 | Bentell | 128/770 |
| 3,734,080 | 5/1973 | Petterson et al. | 128/764 |
| 3,797,491 | 3/1974 | Hurschman | 604/51 |
| 3,960,139 | 6/1976 | Bailey | 128/765 |
| 3,985,122 | 10/1976 | Topham | 128/765 |
| 4,240,411 | 12/1980 | Hosono | 128/4 |
| 4,267,846 | 5/1981 | Kontos | 128/765 |
| 4,299,238 | 11/1981 | Baidwan et al. | 128/763 |
| 4,360,016 | 11/1982 | Sarrine | 128/770 |
| 4,441,570 | 4/1984 | Worley et al. | 128/763 |
| 4,493,700 | 1/1985 | Cassow et al. | 604/55 |
| 4,542,749 | 9/1985 | Caselgrandi et al. | 128/763 |

FOREIGN PATENT DOCUMENTS 734384  7/1955  United Kingdom ................ 604/15

Primary Examiner—Kyle L. Howell
Assistant Examiner—Max F. Hindenburg
Attorney, Agent, or Firm—Reising, Ethington, Barnard, Perry & Milton

[57] ABSTRACT

An instrument (10) for obtaining a fetal blood sample including an elongated member (12) having an open end portion (14) and a membrane (16) disposed over the open end portion (14) for perfecting a seal about the open end portion (14). A lancet (18) in the form of a blade (64) or a sharp ended capillary tube (48) is disposed in the elongated member (12) for piercing the membrane (16) and making an incision in the skin of a fetus (20). A plunger (26) is supported within the elongated member (12) and is movable to create a suction within the open end portion (14) to draw fetal blood from the incision through the pierced membrane (16) and into the open end portion (14).

27 Claims, 8 Drawing Figures

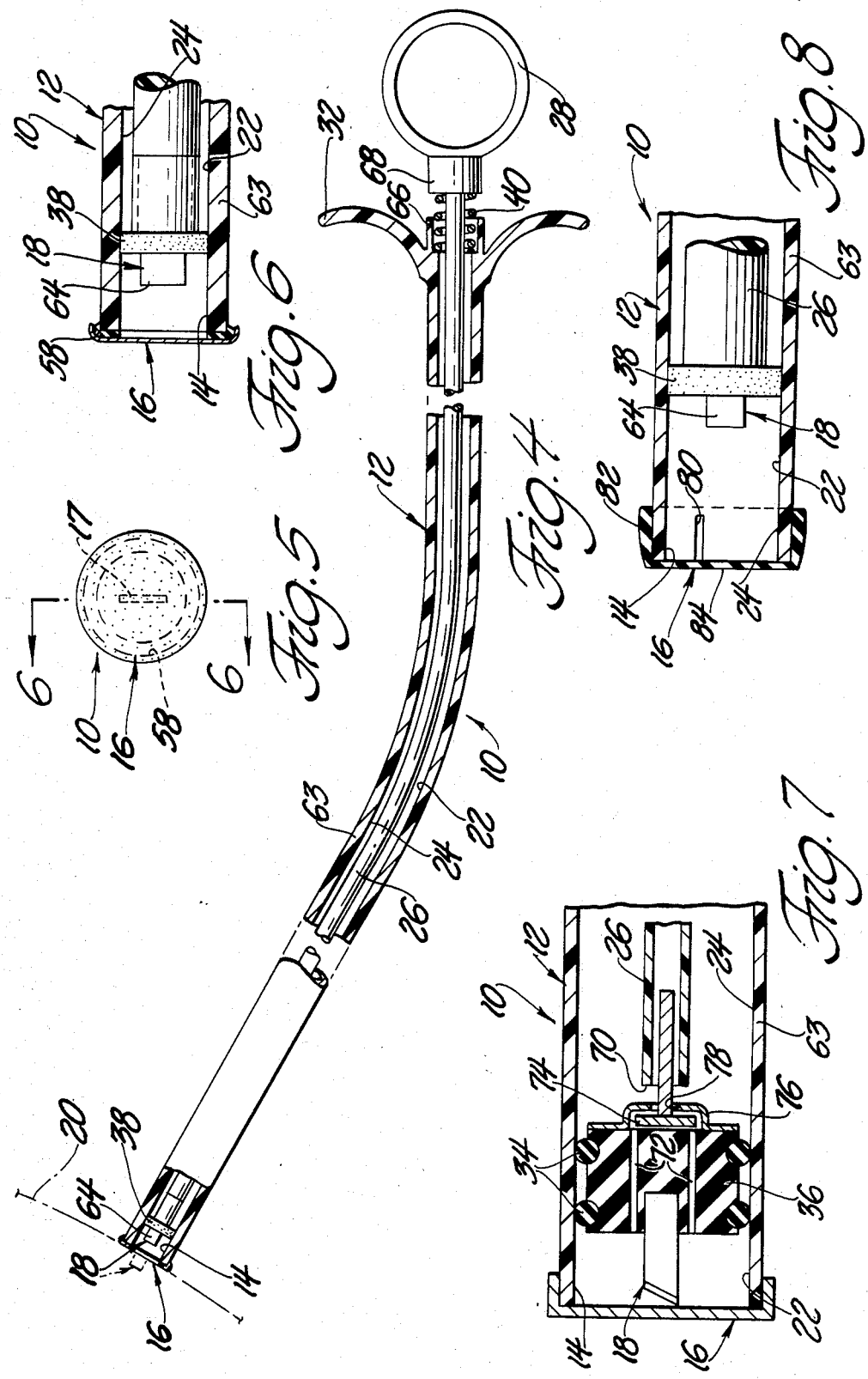

FETAL BLOOD SAMPLING INSTRUMENT

RELATED APPLICATION

This is a continuation of Ser. No. 679,233 filed Dec. 7, 1984, which is a continuation-in-part of Ser. No. 625,738 filed June 28, 1984, both now abandoned.

TECHNICAL FIELD

The subject invention relates to an instrument for obtaining a trans-vaginal fetal blood sample. The instrument is of the type for being inserted vaginally into contract with the presenting fetal skin during labor and for lancing the skin to a predetermined depth and drawing blood from the incision into the instrument to provide a blood sample ready for testing.

BACKGROUND ART

The accepted method of identifying intrauterine fetal asphyxia is by fetal blood sampling to determine the blood pH. Present techniques require the direct trans-vaginal visualization of the fetal scalp or other presenting part using a fetal endoscope and an external light source. The skin is first cleansed with a swab to remove meconium and amniotic fluid and is then incised with a lancet until a free flow of blood occurs. A quick striking motion of the instrument is required to cut the skin. After the lancet is withdrawn, a capillary tube is inserted to draw off the blood sample. There are no means for retaining the endoscope in place during this procedure. This procedure is difficult, time consuming, extremely uncomfortable for the mother, and cannot normally be used during the early stages of labor.

A blood collecting device is disclosed in the U.S. Pat. No. 4,360,016 to Sarrine, issued Nov. 23, 1982. The blood collecting device includes a lancet and capillary tube carried together by an elongated member. The device positions the capillary tube adjacent the skin when the lancet is advanced by the member to puncture the skin. The entire instrument is moved to force the lancet to cut. In an environment such as the vagina, there is no means for shielding the capillary tube from contaminating fluids prior to contacting a fetus. A separate cone is used as a shield. The cone is first inserted and pressed against the fetal scale. The cone may cut off circulation to the isolated area making sampling difficult. Removal of the cone may return circulation to the lanced area thereby initiating excessive post sampling bleeding.

The U.S. Pat. No. 1,147,408 to Kells, issued July 20, 1915 discloses a trocar type device including means for providing a suction for drawing bodily fluid from a cavity through the puncturing trocar. The Kells patent also discloses no means for shielding the device prior to contact with the skin to be punctured. Nor could this device be applied trans-vaginally onto the fetal presenting part for the acquisition a fetal blood sample.

These prior art assemblies for lancing or puncturing skin and the drawing a blood or bodily fluid sample therefrom, when used alone, include no means for shielding the device from the environment nor do they include any means for retaining the assembly in place during the drawing of the blood sample. As disclosed in the Sarrine patent, a conventional endoscope must be used to provide a pathway through which the blood collecting device is used. This method uses a plurality of devices and still does not provide the desired environment.

STATEMENT OF THE INVENTION

According to the present invention, there is provided an instrument for obtaining a fetal blood sample including an elongated member having an open end portion and membrane means disposed over the end portion for perfecting a seal about the open end portion. Lancing means slidably supported within the elongated member pierces the membrane and makes an incision in the skin of the fetus. Suction means creates a suction within the open end portion to draw fetal blood from the incision through the pierced membrane and into the open end portion and retains the instrument over the incision.

The present invention further provides a method for obtaining a fetal blood sample including the steps of inserting the open end portion of a blood sampling instrument trans-vaginally to contact the presenting skin of the fetus, inserting a lancet intradermally to make an incision in the skin of the fetus, removing the lancet from the incision while simultaneously creating a suction to retain the open end portion over the incision, and drawing blood from the incision by continuing the suction.

The membrane means provides a shield over the open end portion thereby preventing contamination of the open end portion during insertion and withdrawal of the instrument through the vagina to the fetal presenting part. Suction is created to draw in the fetal blood sample as the device contacts the fetal skin.

FIGURES IN THE DRAWINGS

Other advantages of the present invention will be readily appreciated as the same becomes better understood by reference to the following detailed description when considered in connection with the accompanying drawings wherein:

FIG. 4 is a side view partially broken away of a second embodiment of the instant invention;

FIG. 5 is an enlarged end view of the instrument shown in FIG. 4;

FIG. 6 is an enlarged fragmentary cross sectional view taken along lines 6—6 of FIG. 5;

FIG. 7 is a fragmentary cross sectional view of a valve means constructed in accordance with the instant invention; and FIG. 8 is a fragmentary cross sectional view of a second embodiment of the valve means constructed in accordance with the instant invention.

DETAILED DESCRIPTION OF THE DRAWINGS

Figure 1:
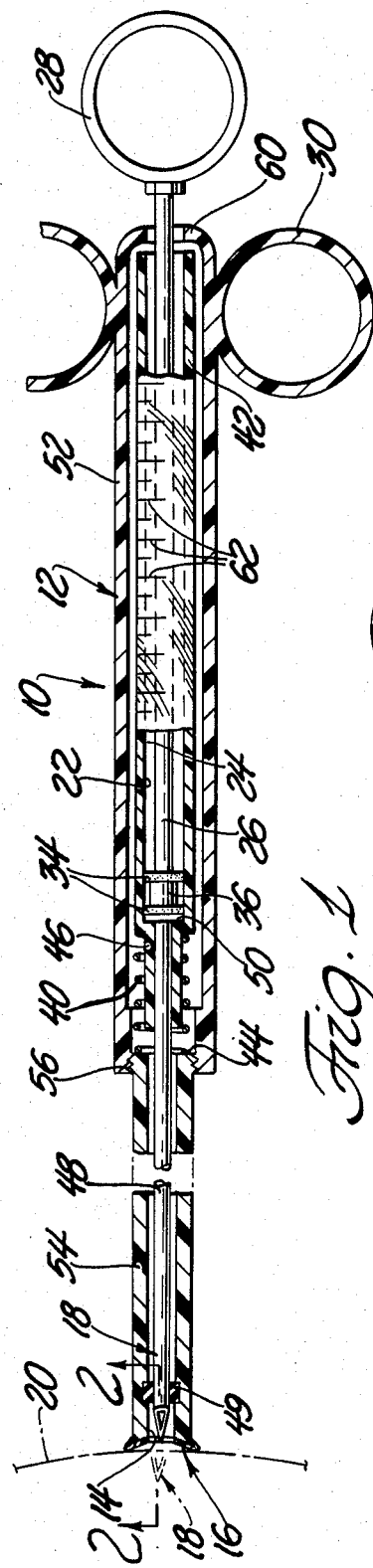
FIG. 1 is a longitudinal cross sectional view partially broken away of an instrument constructed in accordance with the instant invention.

An instrument for obtaining a fetal blood sample constructed in accordance with the instant invention is generally shown at 10 in the Figures. Like numerals are used to designate like structures among the several embodiments.

The instrument includes an elongated member generally indicated at 12. The elongated member 12 has an open end portion 14. Membrane means generally indicated at 16 is disposed over the end portion 14 for perfecting a seal about the open end portion 14. Lancing means generally indicated at 18 is slidably supported within the elongated member 12 for piercing the membrane means 16 and making an incision in the skin of a fetus 20. Suction means creates a suction within the open end portion 14 to draw fetal blood from the incision through the pierced membrane means 16 and into the open end portion 14 for collection of a blood sample. Simultaneously, the suction retains the open end portion 14 at the incision site and promotes bleeding by physically opening the incision slightly as the skin is slightly pulled into the open end portion by the suction. The membrane means 16 may be made from a tissue-like diaphragm. As the elongated member 12 is inserted trans-vaginally, the membrane means 16 prevents the entrance of meconium and amniotic fluid into the open end portion 14. The membrane means 16 is not to be pierced until placed directly adjacent the fetal scalp 20 or other tissue. The lancing means 18 pierces the membrane means 16. While the membrane means 16 is retained against the incision, the suction means draws the blood sample through the pierced membrane means 16 so as to be collected in the open end portion 14. The instrument 10 is then withdrawn, the membrane means preventing the entrance of contaminating fluids into the open end portion 14 during the withdrawl.

Figure 3:
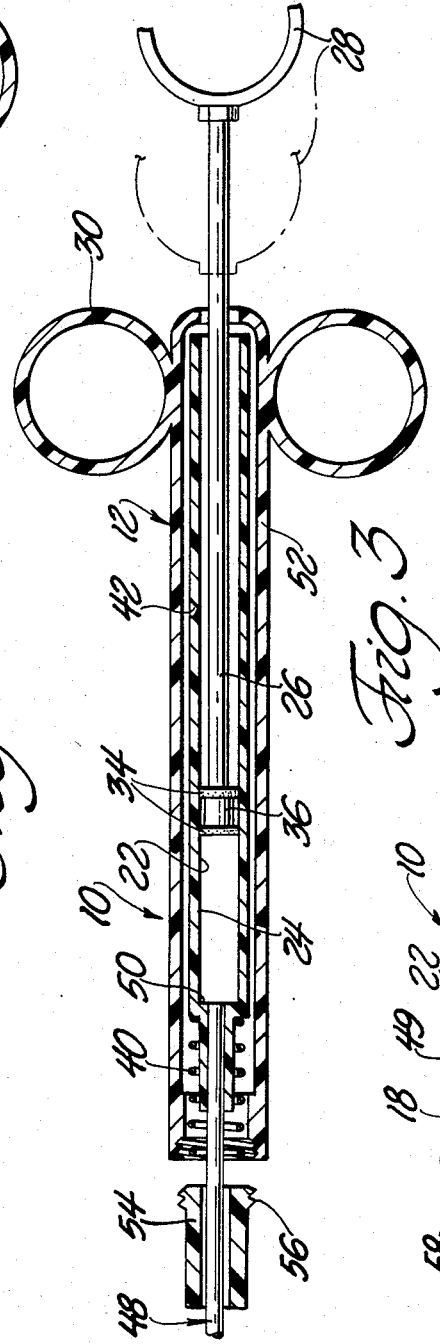
FIG. 3 is a longitudinal cross sectional view of the instrument shown in FIG. 1 wherein the instrument is partially disassembled.

More particularly, the elongated member 12 includes an inner chamber 22 having an inner wall 24. The inner chamber 22 in its entirety includes the open end portion 14. A plunger 26 is slidably supported within the inner chamber 22. The plunger 26 may have a ring 28 or other type of gripping device mounted on the end thereof. The elongated member 12 includes rings 30 as an integral part thereof to be gripped by the fingers of a user. Alternatively, the elongated member 12 may have handles 32 as shown in FIG. 4. The suction means includes sealing means mounted on the plunger 26 and slidably engaging the inner wall 24 to perfect a seal therewith whereby retraction of the plunger 26 moves the sealing means to create suction within the open end portion 14 to draw fetal blood through the pierced membrane means 16 and into the open end portion 14. As shown in FIGS. 1, 3 and 7, the sealing means includes a pair of gaskets 34 disposed about a piston 36 mounted on the end of the plunger 26. Alternatively, a single gasket 38 may be disposed about an end portion of the plunger 26 as shown in FIGS. 4, 6 and 8. The gaskets 34 and 38 slidably engage the inner wall 24 thereby perfecting a sliding seal therewith.

The plunger 26 is slidably supported between a depressed position as shown in phantom in FIGS. 1 and 4 wherein the lancing means 18 extends through the membrane means 16 and a retracted position shown in solid lines in FIGS. 1 and 4 wherein the lancing means 18 is disposed within the open end portion 14 of the elongated member 12. The instrument 10 includes biasing means comprising a spring 40 for biasing the plunger 26 to the retracted position.

The plunger 26 is slidably mounted for movement to a third position shown in FIG. 3 in solid lines from the retracted position shown in FIG. 3 in phantom, the third position being beyond the retracted position, to move the sealing means to create a suction within the open end portion 14 thereby drawing fetal blood through the pierced membrane means 16 and into the open end portion 14. Simultaneously, the suction effect retains the instrument 10 at a single spot on the skin surface. Unlike prior art assemblies which could move away from the cut skin, the instant invention is retained there by the suction effect. In other words, the movement of the plunger 26 between the retracted and depressed positions will puncture through the membrane means 16. Drawing the plunger 26 to the third position beyond the retracted position moves the sealing means 34,38 to create a vacuum within the open end portion 14 thereby creating a vacuum force to draw a blood sample into the open end portion 14. The suction will also draw the skin slightly into the open end portion thereby opening the incision slightly to promote bleeding.

Figure 2:
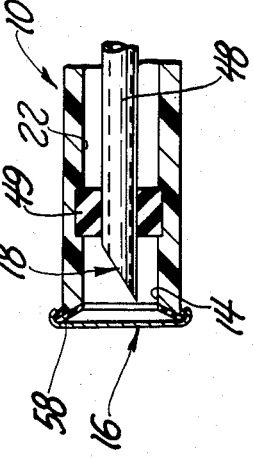
FIG. 2 is an enlarged cross-sectional view taken on line 2—2 of FIG. 1.

The instrument 10 includes motion limiting means for limiting the motion of the plunger 26 between the retracted and depressed positions. As shown in the embodiment of FIGS. 1-3, the elongated member 12 includes a first sleeve 52 housing the guide tube 42 and the plunger 26. A second sleeve 54 has one end 56 detachably connected to the first sleeve 52 by threads as shown or by other suitable means and a second end defining the open end portion 14. The membrane means 16 is disposed over the open end portion 14, the capillary tube 48 being disposed within the second sleeve 54. The motion limiting means may include a guide tube 42 slidably housed within the sleeve 52. The second sleeve 54 includes an end portion defining a shoulder portion 44 when connected to the first tube 52. The plunger 26 is housed within the guide tube 42 for movement therewith between the depressed position wherein the guide tube 42 engages the shoulder portion 44 and the retracted position wherein the guide tube 42 is spaced axially from the shoulder portion 44 and engages a lip 60 on sleeve 52. The biasing member or spring 40 as shown in FIGS. 1 and 3 is disposed between the guide tube 44 and the shoulder portion 46 for biasing the guide tube 44 and the plunger 26 housed therein to the retracted position. The spring 40 is disposed about a constricted portion 46 of the guide tube 42.

The embodiment shown in FIGS. 1 and 3 includes a heparinized capillary tube 48 and capillary tube support means comprising the constructed portion 46 of the guide tube 42 for slidably supporting the capillary tube 48 within the elongated member 10. The capillary tube 48 has a sharp end portion defining the lancing means 18. The end of the capillary tube 48 is sealed by an O-ring or gasket 49. The capillary tube 48 is operatively connected to the plunger 26 by being fit into the constructed portion 46 of the guide tube 42 and is moveable therewith between the depressed position wherein the sharp end portion of the capillary tube 48 extends through the membrane means 16 a predetermined distance and the retracted position wherein the sharp end portion of the capillary tube 48 is disposed within the open end portion 14 of the second sleeve 54.

The constricted end portion 46 of the guide tube 42 merges with the remainder of the guide tube 42 at a second shoulder portion 50. The plunger 26 is slidably moveable within the guide tube 42 to the third position wherein the sealing means is axially spaced from the second shoulder portion 50 thereby creating a suction within the capillary tube 48 to draw fluid into the capillary tube 48. The gasket 49 seals the end of the capillary tube 48 to the second sleeve 54 thereby limiting the potential volume of the end portion 14. Thusly, the blood sample is drawn into the capillary tube 48 and is not consumed by the volume of the remainder of the second sleeve 54.

Since no external light source is needed for use of the instrument 10, it can be made to a relatively small outside diameter; for example, on the order of about 7 millimeters. Since the diameter of the membrane means 16 is quite small, the initial engagement thereof with the fetal skin will dispense or push away any meconium or amniotic fluid on the skin from the area to be incised.

In use, the instrument 10 is inserted vaginally until the membrane means 16 is seated against the fetal scalp or other presented part. The contacting of the open end portion 14 with the presenting skin creates a seal therebetween thereby preventing the entrance of external matter. The plunger 26 is then depressed to propel the sharp end portion of the capillary tube 48 through the membrane means 16 and into the skin to a predetermined depth. As shown in the enlarged view in FIG. 2, a gasket 58 may be used to support the membrane means 16. Thusly, the gasket 58 would be pressed against the fetal scalp, the gasket 58 creating a seal with the scalp. The depth of the incision is preferably about 2 millimeters and is controlled by the engagement of the end of the constricted portion 46 of the guide tube 42 against the shoulder 44 formed by the end portion of the second sleeve 54. The spring 40 normally holds the guide tube 42 and the capillary tube 48 in a position such that the sharp end portion of the capillary tube 48 is positioned just inwardly of the membrane means 16, thus a total movement of the plunger 26 of about three millimeters should be provided. After the incision is made and the plunger 26 is released, the spring 40 will retract the capillary tube 48 until the guide tube 42 engages a lip 60 on the first sleeve 52. The plunger 26 is then pulled to create a suction within the open end portion 14. Since the inner end of the capillary tube 48 opens into the inner chamber 22, the suction will be applied at the outer end of the capillary tube 48 and at the incision in the fetal skin to promote the flow of blood into the capillary tube 48. The suction additionally aids to hold the instrument 10 firmly against the skin 20 to insure the flow of blood into the instrument 10. The membrane means 16 prevents contamination of the instrument 10 by meconium or amniotic fluid as the instrument 10 is being removed or inserted vaginally against the fetal presenting part. If desired, the guide tube 42 may be provided with markings 62 to indicate the extended movement of the plunger 26 and thus the amount of blood to be drawn.

After the desired sample is taken, the instrument 10 is withdrawn. The second sleeve 54 is disconnected from the remainder of the instrument 10, as shown in FIG. 3. This exposes the capillary tube 48 which can then be immediately inserted into a blood analysis device.

A second embodiment of the instant invention is shown in FIGS. 4, 5 and 6. The instrument 10 includes an elongated member 12 comprising a single sleeve 63. The sleeve 63 may be curved or bent at about a 30 degree angle to fit the pelvic curve. The instrument 10 shown in FIGS. 1 through 3 may also have a similar curvature.

The open end portion 14 of the sleeve 63 has a gasket 58 and membrane means 16 as previously described. At its peripheral end, the plunger 26 carried a knife blade or lancet 64. The spring 40 is mounted between the end of the sleeve 63 and supported within a cylindrical flange 66 and abuts against a collar 68 which supports the ring member 28 on the plunger 26. The spring 40 reacts against the sleeve 63 and collar 68 to hold the plunger 26 in its normally retracted position shown with the lancet 64 positioned inwardly of the membrane means 16. The open end portion 14 of the sleeve 63 heparinized to prevent clotting of the blood sample.

In use, the plunger 26 is depressed to move the blade 64 through the membrane means 16 and into the fetal skin 20 to a depth predetermined by the engagement of the collar 68 with the cylindrical flange 66 thereby defining the motion limiting means. Release of the plunger 26 will allow the spring 40 to retract the plunger 26 to its original retracted position. Further movement of the ring 28 to a third position will create suction within the open end portion 14 to improve the flow of blood into the open end portion 14. The initial movement of the plunger 26 to its retracted position by the spring will draw a small blood sample into the instrument 10 by creating some suction at the open end portion 14. If the plunger 26 is pulled further out to the third position, a larger sample will be withdrawn. Graduations on the sleeve 63 may be provided to indicate the amount of blood taken. When the instrument 10 is withdrawn, a capillary tube (not shown) is used to draw off blood from the open end portion 14 and the capillary tube (not shown) would then be inserted into the testing equipment.

The instrument 10 may include valve means as shown in FIG. 7 for allowing removal of the instrument after sampling without drawing vaginal fluid therein. The valve means has an open condition for allowing air to exit from the open end portion 14 as the plunger 26 is moved from the retracted position to the depressed position prior to puncturing the membrane means 16 at 17. This allows a rapid forward motion of the lancet 18 which facilitates and insures incision of the fetal skin. The valve means also has a closed condition preventing air flow into the open end portion 14 as the plunger 26 is moved to the retracted position thereby forming a suction within the open end portion 14 to draw the blood sample into the open end portion 14 through the pierced membrane means 16. The valve means releases the vacuum to allow removal of the instrument without any further suction.

A first embodiment of the valve means is shown in FIG. 7. The plunger 26 includes a hollow end portion 70 and a piston 36 mounted thereon. The sealing means comprises two gaskets 34 which are disposed about the piston 36 in sliding sealing engagement with the inner wall 24 of the inner chamber 22. The piston 36 has openings or passageways 72 extending therethrough for air communication between open end portion 14 and the remainder of the inner chamber 22. The valve means includes a plug member 74 mounted on the end 70 of the plunger 26 and a boot 76 mounted on the piston 36 over the openings 72 and having a boot opening 78. The plug member 74 is slidably retained within the boot opening 78 for engaging the boot 76 to sealingly close the boot opening 78 as the plunger 26 is retracted and for being spaced from the boot opening 78 as the plunger 26 is depressed. Pulling on the plunger 26 closes the valve assembly allowing the formation of a vacuum in the open end portion 14 thereby drawing the blood sample into the open end portion 14 through the slit 17 in the membrane means 16. Pressing the plunger 26 opens the valves means allowing excess air from the open end portion 14 to escape. Releasing tension on the plunger 26 allows air to enter the open end portion 14 eliminating the vacuum which decreases the chance of contamination into the open end portion 14 as the instrument is pulled away from the fetal part.

An alternative embodiment is shown in FIG. 8. The inner wall 24 of the open end portion 14 includes a slot 80 extending therethrough. The valve means includes a flexible gasket 82 disposed over the slot 80 whereby the gasket 82 allows one way out flow of air from the open end portion 14 through the slot 80 during movement of the plunger 26 to the depressed position while sealing off the slot 80 preventing inflow of fluid contaminants through the slot 80 as the plunger 26 is moved to the retracted position. More particularly, the membrane means 16 includes a cupped shaped elastic member including a thin tissue-like base portion 84 disposed over the open end portion 14 of the elongated member 12 and thicker annual wall portion defining the gasket 82 and being disposed over the slot 80.

In use, depressing the plunger 26 causes an increase of pressure in the open end portion 14. The slot or notch 80 in the open end portion 14 allows escape of air. The gasket 82 over the slot 80 acts as a one-way valve allowing a vacuum to form in the open end portion 14 when the plunger 26 is pulled.

Due to the inherent disadvantages of the fetal blood sampling instruments currently in use, the procedure is under-utilized, which may result in unnecessary caesarean sections due to misdiagnosis of fetal distress and asphyxia. In addition, undiagnosed cases of true fetal asphyxia result in an increase in fetal mortality and morbidity which might be avoided by timely caesarean delivery. The instrument described herein possesses many advantages over currently used instruments and the procedures they require, among which are: ability to obtain blood samples at a relatively early stage of labor which may reduce the incidence of brain damage and the incidence of unnecessary caesarean sections; the procedure is simple to perform and requires only one physician; a smaller incision is possible because suction aids bleeding; less discomfort for the patient; and it does not require a fetal endoscope or direct vision of the fetal part, rather, this device is applied onto the fetal part by palpation.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An instrument (10) for obtaining a fetal blood sample comprising: an elongated member (12) having an open end portion (14), said open end portion (14) being hollow; tissue thin membrane means (16) disposed in sheet-like fashion over said open end portion (14) for perfecting a seal about said open end portion (14) to close said open end portion (14) to outside contaminants; lancing means (18) slidably supported within said elongated member (12) for piercing said membrane means (16) and making an incision in the skin (20); and suction means for creating a suction within said open end portion (14) while maintaining the open end portion (14) and pierced membrane means (16) thereunder sealed against the skin and from outside contaminants to draw blood from the incision in the skin through said pierced membrane means (16) and into said hollow open end portion (14), gripping means (28,30,32) for holding the open end portion (14) and pierced membrane means (16) sealed against the skin while moving said lancing means (18) outward to pierce said membrane means (16) and adjacent skin and while withdrawing said lancing means (18) back out of the incision and said membrane means (16) and into said open end portion (14) and while actuating said suction means to draw blood into said open end portion (14).

2. An instrument as set forth in claim 1 wherein said elongated member (12) includes an inner chamber (22) having an inner wall (24) and including said open end portion (14), said instrument (10) including a plunger (26) slidably supported within said inner chamber (22), said suction means including sealing means mounted on said plunger (26) and slidably engaging said inner wall (24) to perfect a seal therewith whereby retraction of said plunger (26) moves said sealing means to create a suction within said open end portion (14) thereby drawing fetal blood through said pierced membrane means (16) and into said open end portion (14).

3. An instrument as set forth in claim 2 wherein said sealing means includes at least one annular gasket (34,38) disposed around a portion (36) of said plunger (26), said gasket (34,38) slidably engaging said inner wall (24) thereby perfecting a sliding seal therewith.

4. An instrument as set forth in claim 3 wherein said plunger (26) is slidably supported between an inserted position extending said lancing means (18) through said membrane means (16) and a retracted position wherein said lancing means (18) is disposed within said open end portion (14), said instrument (10) including biasing means (40) for biasing said plunger (26) to said retracted position.

5. An instrument as set forth in claim 4 wherein said plunger (26) is slidably mounted for movement to a third position beyond said retracted position to move said sealing means to create a suction within said open end portion (14) thereby drawing fluid through said pierced membrane means (16) and into said open end portion (14).

6. An instrument as set forth in claim 5 including motion limiting means for limiting the motion of said plunger (26) between said depressed and retracted positions.

7. An instrument as set forth in claim 6 wherein said motion limiting means including a guide tube (42) slidably housed within said elongated member (10) and a shoulder portion (44) extending into said inner chamber (22), said plunger (26) being housed within said guide tube (42) for movement therewith between said inserted position wherein said guide tube (42) engages said shoulder portion (44) and said retracted position wherein said guide tube (42) is axially spaced from said shoulder portion (44).

8. An instrument as set forth in claim 7 wherein said biasing means comprises a biasing member (40) disposed between said guide tube (42) and said shoulder portion (46) for biasing said guide tube (42) and said plunger (26) housed therein to said retracted position.

9. An instrument as set forth in claim 8 including a capillary tube (48) and capillary tube support means for slidably supporting said capillary tube (48) within said elongated member (10), said capillary tube (48) having a sharp end portion defining said lancing means (18), said capillary tube (48) being operatively connected to said plunger (26) and movable therewith between said depressed position wherein said sharp end portion extends through said membrane means (16) a predetermined distance and said retracted position wherein said sharp end portion is disposed within said open end portion (14) of said elongated member (12).

10. An instrument as set forth in claim 9 wherein said elongated member (12) includes a first sleeve (52) housing said guide tube (42) and said plunger (26), said elongated member (12) including a second sleeve (54) having one end detachably connected to said first sleeve (52) and a second end defining said open end portions (14) having said membrane means (16) disposed thereover, said capillary tube (48) being disposed within said second sleeve (54), said assembly 10 including potential volume limiting means within said second sleeve (54) for limiting the potential volume of said open end portion (14) whereby the blood sample is drawn into said capillary tube (48) rather than being consumed by the volume of said open end portion (14).

11. An instrument as set forth in claim 10 wherein said potential volume limiting means includes an O-shaped gasket (49) disposed about said capillary tube (48) and in sealing engagement with said inner wall of sleeve (54) thereby perfecting a seal therebetween.

12. An instrument as set forth in claim 9 wherein said capillary tube support means includes a constricted end portion (46) of said guide tube (42) for frictionally retaining said capillary tube (48) therein.

13. An instrument as set forth in claim 9 wherein said constricted end portion (46) of said guide tube (42) merges with the remainder of said guide tube (42) at a second shoulder portion (50), said plunger (26) being slidably movable within said guide tube (42) to said third position wherein said sealing means is axially spaced from said second shoulder portion (50) thereby creating a suction within said capillary tube (48) to draw fluid into said capillary tube (48).

14. An instrument as set forth in claim 2 including valve means having an open condition for allowing air to escape out of said open end portion (14) as said plunger (26) is moved from said retracted position to said depressed position prior to puncturing said membrane means (16) and said valve means having a closed condition preventing air flow into said open end portion (14) as said plunger (26) is moved to said retracted position thereby forming a suction within said open end portion (14) to draw fetal blood into said open end portion (14) through said pierced membrane means (16).

15. An instrument as set forth in claim 14 wherein said plunger (26) includes an end portion (70) and a piston (36), said sealing means being disposed about said piston (36) in slidably sealing engagement with said inner wall (24) of said inner chamber (22), said piston (36) having at least one opening (72) extending therethrough for air communication between said open end portion (14) and the remainder of said inner chamber (22), said valve means including a plug member mounted on the end portion (70) of said plunger (26) and a boot (76) mounted on said piston (36) over said openings (72) and having a boot opening (78), said plug member (74) being slidably retained within said boot opening (78) for engaging said boot (76) to sealingly close said boot opening (78) as said plunger (26) is retracted and for being spaced from said boot opening (78) as said plunger (26) is inserted.

16. An instrument as set forth in claim 14 wherein said inner wall (24) of said open end portion (14) includes at least one slot (80) extending therethrough, said valve means including a flexible gasket (82) disposed over said slot (80) whereby said gasket (82) allows one way outflow of air from said open end portion (14) through said slot (80) during movement of said plunger (26) to said depressed position while sealing off said slot (80) preventing inflow of fluid through said slot (80) as said plunger (26) is moved to said retracted position.

17. An instrument as set forth in claim 16 wherein said membrane means (16) includes a cup shaped elastic membrane including a thin tissue-like base portion (84) disposed over said open end portion (14) of said elongated member (12) and a thicker annular wall portion defining said gasket (82) and being disposed over said slot (80).

18. An instrument as set forth in claim 2 wherein said lancing means (18) including a lancet blade (64) mounted on the end of said plunger (26).

19. An instrument as set forth in claim 9 wherein said elongated member comprises a single sleeve (63).

20. An instrument as set forth in claim 19 wherein said sleeve (63) includes a cup shaped end portion (66) opposite said open end portion (14), said plunger (26) including bias abutment member (68) for engaging said biasing means (40), said biasing member (40) being mounted on said plunger (26) between said cup shaped end portion (66) and said abutment means (68).

21. A method for obtaining a blood sample comprising the steps of: disposing a tissue thin membrane means (16) over the open hollow end portion (14) of a blood sampling instrument (10) to close the open end portion (14) to outside contaminants; inserting the open end portion (14) to contact the presenting skin with the membrane means (16) pressed against the skin by the open end portion (14); inserting a lancet (18) from within the open end portion (14) of the instrument (10) intradermally to make an incision in the membrane means (16) and the skin; removing the lancet (18) from the incision and the membrane means (16) and into the instrument (10) while maintaining the pierced membrane means (16) and open end portion (14) sealed against the skin; and creating a suction within the open end portion (14) of the instrument (10) to draw blood into the open end portion (14) from the incision in the skin and through the pierced membrane (16) by continuing said suction.

22. A method for obtaining a fetal blood sample as set forth in claim 21 including the steps of releasing the suction once the sample is drawn and removing the instrument (10).

23. A method for obtaining a fetal blood sample as set forth in claim 22 wherein a membrane (16) is disposed over the open end portion (14), said method further defined by contacting the membrane (16) to the presenting fetal skin, piercing the membrane (16) with the lancet (18) as the lancet (18) then cuts the fetal skin, and drawing the blood from the incision and through the membrane (16).

24. A method for obtaining a fetal blood sample as set forth in claim 23 wherein the step of releasing the suction is further defined by sealing off the open end portion (14) with the membrane (16) as the suction is released and withdrawing the sealed open end portion (14) from the incision.

25. A method for obtaining a fetal blood sample as set forth in claim 21 wherein the step of drawing blood is further defined as increasing the suction a predetermined amount to create a vacuum within the open end portion (14) to draw a predetermined amount of blood.

26. A method for obtaining a fetal blood sample as set forth in claim 21 wherein the instrument in inserted trans-vaginally to contact the presenting skin by palpation.

27. A method for obtaining a fetal blood sample as set forth in claim 21 further including the step of physically opening the incision in the skin by the suction slightly pulling the skin into an open end portion (14).

* * * * *